United States Patent [19]

Prosperi et al.

[11] Patent Number: 6,063,602

[45] Date of Patent: May 16, 2000

[54] LIPOPOLYSACCHARIDE BIOSURFACTANT

[75] Inventors: Giulio Prosperi, Rome; Marcello Camilli, Grotta Ferrata; Francesco Crescenzi, Rome; Eugenio Fascetti, Rome; Filippo Porcelli, Rome; Pasquale Sacceddu, Monterotondo (Rome), all of Italy

[73] Assignee: EniTecnologie S.p.A., San Donato Mil.se, Italy

[21] Appl. No.: 09/212,409

[22] Filed: Dec. 16, 1998

[30] Foreign Application Priority Data

Dec. 19, 1997 [IT] Italy .................................. MI97A2809

[51] Int. Cl.[7] .............................. C12P 19/26; C11D 3/22; B01F 17/30; B01F 17/16

[52] U.S. Cl. .................................. 435/84; 435/72; 435/74; 435/135; 435/170; 435/252.1; 435/101; 510/470; 510/471; 516/69; 516/70; 516/72; 516/73; 516/203; 516/204; 516/914; 516/915; 516/917; 516/918

[58] Field of Search .................................. 435/72, 74, 135, 435/170, 252.1, 101, 84; 252/356, 357; 510/470, 471; 516/69, 70, 72, 73, 203, 204, 914, 915, 917, 918

[56] References Cited

U.S. PATENT DOCUMENTS 4,395,354   7/1983   Gutnick et al. .......................... 252/356

OTHER PUBLICATIONS

Kropinski et al, Antimicrob. Agents. Chemother., 21(2):310–319, 1982.
Pier et al, J. Clin. Invest., 77:491–495, 1986.
Sonesson et al, Arch. Microbiol., 162:215–221, 1994.
Kawahara et al, Eur. J. Biochem., 163:489–495, 1987.
Rosenberg et al, Appl. Environ. Microbiol., 54(2):323–326, 1988.
Haseley et al, Eur. J. Biochem., 250:617–623, 1997.

*Primary Examiner*—Francisco Prats
*Attorney, Agent, or Firm*—Oblon, Spivak, McClelland, Maier & Neustadt, P.C.

[57] ABSTRACT

The invention relates to a new lipopolysaccaride biosurfactant, a strain of *Acinetobacter calcoaceticus* which produces this biosurfactant, and a process for its preparation. The biosurfactant has a high emulsifying capacity, it promotes the biodegradation of hydrocarbons in water and favors the adhesion of microorganisms to the water/oil interface.

22 Claims, 4 Drawing Sheets

LIPOPOLYSACCHARIDE BIOSURFACTANT

The present invention relates to a new lipopolysaccharide biosurfactant, a strain of *Acinetobacter calcoaceticus* which produces this biosurfactant, a process for the preparation of the biosurfactant and its use in energy and environmental fields.

Phenomena resulting from the leakage of hydrocarbon pollutants in water environments are well known. The main mechanism with which the ecosystem reacts to pollution by hydrocarbons consists of biodegradation by the hydrocarbonclastic flora.

Petroleum, which under normal conditions is a liquid which is substantially immiscible in water, tends to spread over the surface of the water in the form of a fine layer ("stain").

With respect to biodegradation any phenomenum capable of breaking and dispersing the "stain" should be considered as being positive. In fact, a partial solubilization or adhesion on solid particles in suspension or emulsification in water favours the action of microorganisms which are given a wider surface for attachment.

On the basis of these considerations a wide range of synthetic dispersing/emulsifying agents has been produced, whose use however is still the object of contrasting opinions owing to the toxicity and persistence in the environment of these products.

This explains why the possibility of using biosurfactants of a microbic origin has been widely studied in the last few years. In fact, biosurfactants are biodegradable and are therefore potentially less toxic than the synthetic compounds used at present.

A group of biosurfactants of particular interest is represented by lipopolysaccharide biopolymers produced from strains of *Acinetobacter calcoaceticus*.

At present the only product available on the market is Emulsan, a polyanionic lipopolysaccharide obtained by the fermentation of the strain *Acinetobacter calcoaceticus* RAG1 ATCC 31012 (U.S. Pat. No. 3,941,692, U.S. Pat. No. 4,395,354).

This biosurfactant is responsible for the formation and stabilization of oil/water emulsions and is essentially used for the transportation of heavy crude oils in association with synthetic surface-active agents (PCT WO 8501.889) and for the cleaning of tanks.

Emulsan can also be used in fields such as cosmetics (EP 242.296, DE 3.610.384, JP 62.286.914, JP 62.289.508) and detergents (JP 62.297.397).

It is known that the dispersion of oil in water produced by a biosurfactant, as well as increasing the surface of the water/oil interface, also modifies its characteristics. This can cause a variation in the affinity between the surface of the oil and microorganisms.

In particular it can change the affinity of the hydrocarbonclastic flora whose adhesion to the water/oil interface is an essential assumption for the activation of biodegradation processes.

At present, it is not possible to predict a priori if a dispersing agent improves or inhibits the adhesion of cells to hydrocarbons, mainly because the phenomenum is governed by complex interactions between the cellular membrane and the surface of the oil.

It can be assumed, however, that lipopolysaccharide biosurfactants, owing to their linear structure and high molecular weight, greatly modify the characteristics of the water/oil interface, thus determining a significant variation in the adhesion capacity of microorganisms.

It has in fact been found that the polymeric biosurfactant Emulsan inhibits the adhesion of microorganisms to the water/oil interface [E. Rosenberg et al., Infect. Immun., 39, 1024–1028 (1983)]. In other words the surface of the oil covered with the biosurfactant becomes less analogous to the biomass and reduces the capacity of adhering to it.

It has also been observed that Emulsan reduces the biodegradation of linear alkanes and other saturated hydrocarbons, as well as aromatic compounds, by 50÷90%, on the part of mixed cultures or purified cultures, [J. M. Foght et al., Appl. Environ. Microbiol., 55, 36–42 (1989)].

As a result, this group of emulsifying agents is not suitable for resolving problems of the environmental type which can take place in the case of the leakage of crude oils in water.

It has now been found that it is possible to overcome the disadvantages of the known art described above by the use of a new strain of *Acinetobacter calcoaceticus*.

In particular, this strain produces a hexocellular lipopolysaccharide biosurfactant (herein also indicated with the term EPS) which has an excellent capacity for forming and stabilizing oil/water emulsions and at the same time favours the adhesion of microorganisms to the water/oil interface and promotes the biodegradation of hydrocarbons in water.

Samples of this strain were deposited on 22.07.1997, at the Centraalbureau voor Schimmelcultures (CBS) where they received the deposit number CBS 962.97.

An object of the present invention consequently relates to the strain *A. calcoaceticus* CBS 962.97.

Another object of the present invention relates to a biosurfactant obtained from *A. calcoaceticus* CBS 962.97.

A further object of the present invention relates to a process for the preparation of this biosurfactant characterized by the use of the strain *A. calcoaceticus* CBS 962.97.

Another object of the present invention relates to the use of the biosurfactant thus obtained in energy and environmental fields.

Further objects of the present invention are evident in the following description and examples.

DETAILED DESCRIPTION OF THE INVENTION

Figure 1:
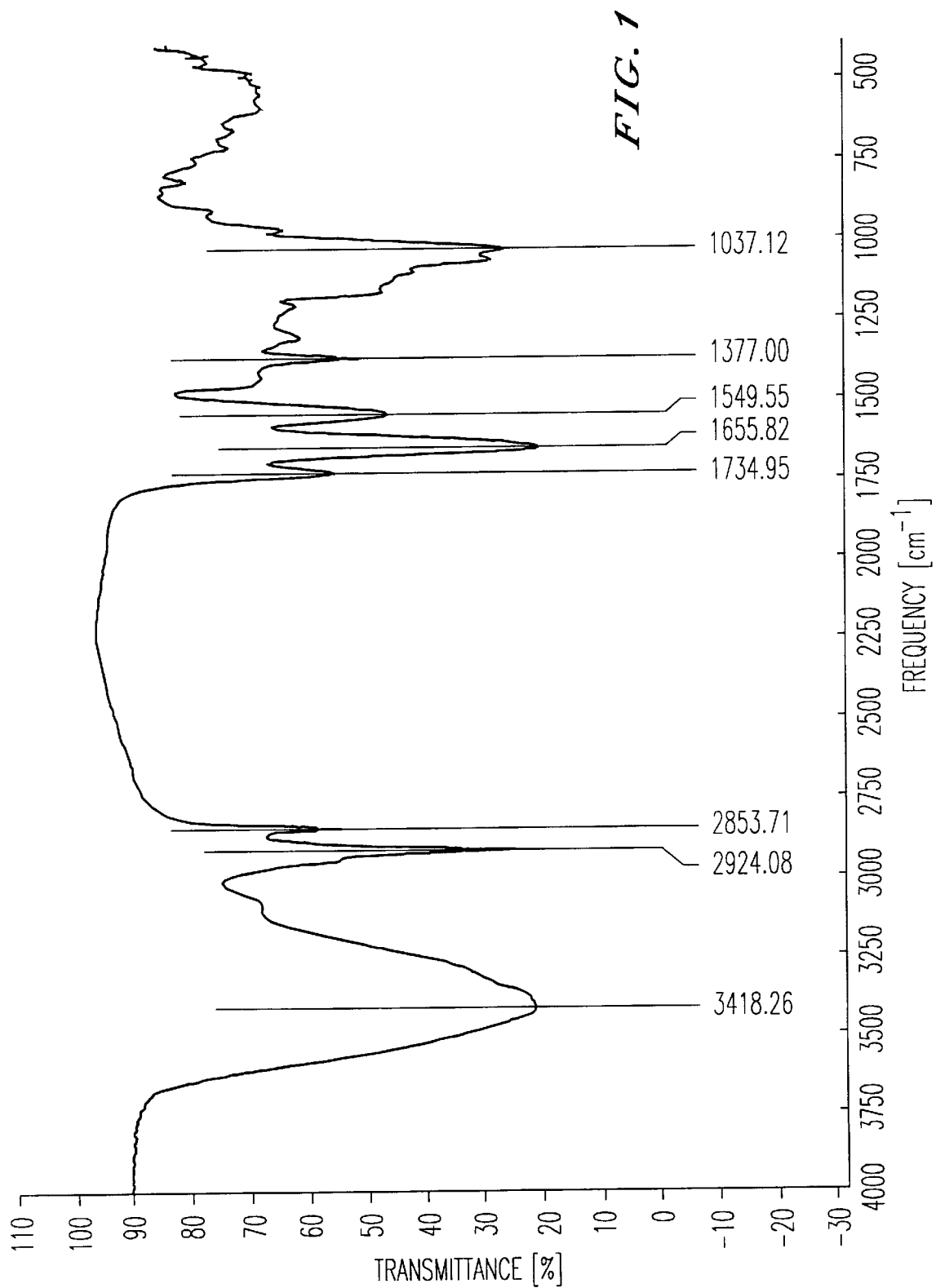
FIG. 1: FT-IR spectrum of EPS II in the solid state in a pellet of KBr.

In order to isolate a biosurfactant-producer microbic strain capable of emulsifying petroleum products, samples of soil taken from sites polluted by hydrocarbons (crude oil, gasoil and gasoline) were used.

The isolation was carried out by successive enrichment and purification phases in saline earth containing a hydrocarbon (for example fuel oil, crude oil, vaseline oil, n-hexadecane or gasoil) as single carbon source according to the Bushnell-Haas method (J. Bateriol., 41, 653–673 (1940)), even though other conventional techniques can be used.

The emulsifying capacity of the various phenotypes was tested, preliminarily, by means of the "crack test" [Krigsvoll et al., "Microbial emulsification of crude oil" in Proceedings of the 5th European Congress in Biotechnology, Vol. I, pages 221–224, Copenhagen, July 1990].

The method consists in putting a pure culture in contact with a hydrocarbon, for example, crude oil, and in verifying the fracture of the oil meniscus which is obtained in the presence of a biosurfactant.

The results obtained showed the presence of a single strain with a high emulsifying capacity. This strain was preliminarily distinguished with the abbreviation ER-96.

For the characterization of the strain ER-96, reference was made to the procedures described in Bergey's Manual of Systematic Bacteriology, Vol I, page 306, Krieg & Holt Eds., 1984, Williams & Wilkins, Baltimore, and in "The Biology of Acinetobacter", Towner, Bergogne-Bérézin and Fewson eds., 1991, Plenum Press, New York. A list of the taxonomical characteristics of the strain ER-96 is provided hereunder:

| A) Morphological and dyeing characteristics | |
|---|---|
| GRAM-reaction | Negative |
| Cellular morphology | Coccoide in a stationary phase |
| Cellular dimensions ($\mu$m) | 0.8 × 1.8 (pleomorph cells) |
| Mobility | Negative |
| Capsule production | Positive |
| B) Cultural characteristics | |
| Colony on Nutrient Agar | Circular |
| Chromogenesis on Agar | Negative |
| Colony elevation | Convex |
| Colony surface | Smooth |
| Colony margin | Whole |
| Colony emulsifiability | Positive |
| Temperature | 30° C. |
| pH | 7. |
| C) Physiological characteristics | |
| Cytochrome-oxidase | Negative |
| Catalase | Positive |
| Ox/F, acc. Leifson | Oxidating |
| Methyl-Red test | Negative |
| Urease | Negative |
| Gelatinase, acc. Kohn | Negative |
| Alkaline phosphatase | Positive |
| Esterase-lipase | Positive |
| Trypsin | Negative |
| Acid phosphatase | Positive |
| Naphthol-phosphohydrolase | Positive |
| $\alpha$-galactosidase | Negative |
| $\beta$-galactosidase | Negative |
| Indole from tryptophan | Negative |
| Acetoine from pyruvate | Positive |
| Reduction Nitrates->Nitrites | Negative |
| Reduction Nitrates->$N_2$ | Negative |
| D) Use of Carbon sources | | | | |
|---|---|---|---|
| Glycerol | − | Arbutin | − | D-Fucose | + |
| Erythritol | − | Esculin | − | L-Fucose | − |
| D-Arabinose | + | Cellobiose | − | L-Arabitol | − |
| Ribose | + | Maltose | − | Gluconate | − |
| D-Xylose | − | Lactose | − | 2-keto-Gluconate | − |
| L-Xylose | − | Melibiose | − | 5-keto-Gluconate | − |
| Adonitol | − | Sucrose | − | Caprate | + |
| Galactose | + | Trealose | − | Adipate | + |
| Glucose | + | Inulin | − | Malate | + |
| Fructose | − | Melezitose | − | Phenyl-Acetate | + |
| Mannose | + | Raffinose | − | Citrate | + |
| Sorbose | − | Soluble starch | − | Ethanol | + |
| Ramnose | − | Glycogen | − | Ca-Acetate | ± |
| Dulcitol | − | Xylitol | − | Hexadecane | + |
| Inositol | − | Gentiobiose | ± | Olive oil | + |
| Mannitol | − | Turanose | − | Tween-80 | + |
| Sorbitol | − | D-Lisose | − | | |
| Amygdalin | − | D-Tagatose | − | | | wherein: + = positive assimilation; − = negative assimilation; ± = weak assimiliation.

On the basis of the results of the morphological, physiological and cultural tests, it was possible to assign the strain ER-96 of the present invention to the Acinetobacter group and, more specifically, to the species *Acinetobacter calcoaceticus*.

Examination of the strain ER-96 also showed characteristics which distinguish it from other strains of *A. calcoaceticus* described in patent literature:

*A. calcoaceticus* RAG-1 (Rosenberg, E.), producer of Emulsan;

*A. calcoaceticus* 217 (Tanaka, Y.), producer of a new biosurfactant (EP-401700).

The characteristics of the strains ER-96, RAG-1 and 217 are indicated in Table 1 below:

TABLE 1

| | ER-96 | RAG-1 | 217 |
|---|---|---|---|
| Average cellular dimensions in $\mu$m (pleomorph cells) | 0.8 × 1.8 | 1.3 × 3.3 | 1.8 × 2.6 |
| Distinctive physiological characteristics | | | |
| gelatinase | − | + | + |
| Reduction nitrates to nitrites | − | + | + |
| Reduction nitrates to $N_2$ | − | n.d. | + |
| Indole production | − | n.d. | + |
| $NH_4^+$ utilization | + | + | − |
| Urease | − | − | + |
| Ox/Ferm. Test | Oxidative | n.d. | Fermentative |
| Lysine decarboxylase | − | n.d. | + |
| Assimiliation of various carbon sources | | | |
| L-Arabinose | + | + | − |
| D-Xylose | − | + | − |
| D-Mannose | + | + | − |
| D-Fructose | − | + | + |
| Galactose | + | + | − |
| D-Maltose | − | + | + |
| Sucrose | − | + | + |
| Trealose | − | + | + |
| D-Mannitol | − | + | + |
| Glycerol | − | + | − | wherein: + = positive activity; − = negative activity;
n.d. = datum not available.

Production and Properties of the biosurfactant

It has been observed that when the strain ER-96 is cultured in a liquid medium using a hydrocarbon such as, for example, n-hexadecane, crude oil, gasoil or other products, as carbon source, this is emulsified as the cells grow.

If the strain ER-96 is cultured using a carbon source which is soluble in water, such as ethanol for example, the emulsification cannot be observed directly, but if hydrocarbons are added to the culture, these are immediately emulsified.

It has also been observed that if the strain ER-96 is cultured using ethanol as carbon source, and during fermentation aliquots of culture broth are taken and the cells removed for example by centrifugation, the surnatant without cells emulsifies the hydrocarbons in a very stable manner and this capacity increases until the end of the fermentation. This result indicates that the biosurfactant produced by the strain ER-96 is released in the fermentation broth.

The emulsions of hydrocarbons in water obtained using the biosurfactant produced by the strain ER-96 remain stable for months. Over a period of time and under static conditions, the dispersed drops or oil rise to the surface owing to the lower density but there is no coalescence and the cream formed can be very easily redispersed.

The production of the biosurfactant can be followed measuring the emulsifying capacity of the fermentation broth.

For this purpose various methods can be used which consist in diluting an aliquot of culture broth, without cells, with water or with a suitable buffer, adding a certain quantity of hydrocarbons, stirring this mixture and measuring the turbidity of the emulsion.

The system, which is extremely reproducible, used in the present invention is a variation of the method described by Gutnick et al. [EP 16.546]: 50 $\mu$l of a mixture of hexadecane and 2-methylnaphthalene (1:1) are added to 3.25 ml of a solution of biosurfactant in tris-hydroxymethylaminomethane 20 mM buffer, pH 7.2, containing $MgSO_4$ 10 mM and the whole mixture is stirred; the optical density of the emulsion is measured at 620 nm in a cuvette with an optical path of 1 cm.

Eniricerche emulsifying capacity Units (1 UE) refers to the quantity of biosurfactant which under the conditions described above, produces an optical density of 1.

The emulsifying capacity specified is consequently defined as the emulsifying capacity of 1 mg of product.

Continuing the research, it was found that by subjecting the fermentation broth without cells and containing the biosurfactant, to dialysis, this does not dialyze, indicating the polymeric nature of this biosurfactant.

The fermentation broth without cells and lyophilized was indicated with the term raw EPS.

To determine the structure and properties of the biosurfactant, this was isolated and purified.

Various techniques can be used for this purpose, such as for example selective precipitation with ammonium sulfate, concentration and desalification of the fermentation broth by means of spiral ultrafiltration membranes such as, hollow fibres or flat membranes, or also selective absorption on a solid carrier.

According to an embodiment of the present invention, the polymeric biosurfactant was precipitated by the addition of ammonium sulfate to the fermentation broth. The precipitate obtained with concentrations of ammonium sulfate ranging from 30 to 40% of the saturation value, recovered by centrifugation, dialyzed against water and lyophilized was called EPS.

This biosurfactant proves to consist of about 20–25% by weight of proteins (Bio-Rad Protein Assay Kit), about 65–70% by weight of a lipopolysaccharide and the remaining percentage of metallic ions, essentially magnesium and sodium.

The specific emulsifying capacity of EPS proved to be 93 UE/mg (corresponding to 428 UG/mg, wherein UG refers to the units as defined by Gutnick et al. [EPA 16546] for Emulsan which corresponds to 330 UG/mg).

Purification and Characterization of the lipopolysaccharide

To enable the physico-chemical and structural characterization of the lipopolysaccharide present in the biosurfactant, the EPS was additionally purified to eliminate any possible contamination on the part of nucleic acids and to separate the lipopolysaccharide from the proteins and metallic ions.

The removal of the nucleic acids can be carried out enzymatically with a nuclease, whereas the proteic fraction can be removed by enzymatic digestion or treatment with warm phenol or by a combination or both.

According to an embodiment of the present invention, the EPS, without nucleic acids, was treated first with a protease and then with warm phenol according to the method of O. Westphal & K. Jann ["Methods in Carbohydrate Chemistry", R.L. Whistler Ed., Vol. V, pages 83–91, Academic Press, New York, 1965].

The aqueous extract was washed with ethyl ether, subsequently dialyzed against water, sodium EDTA, water, NaCl, water, HCl, water, and then lyophilized.

The lipopolysaccharide biosurfactant without proteins was called EPS II.

The specific emulsifying capacity of EPS II proved to be about half (48 UE/mg) of that of EPS.

The physico-chemical characterization of EPS II gave the following results:

a molecular weight, determined by HPLC-SEC (Size Exclusion Chromatography), of about 1,556,400 daltons.

elemental analysis (%): C=44.5; H=7.33; N=4.99; O=40.6; S=0.

Infra-red spectrum (FT-IR).

With reference to FIG. 1: 3418 $cm^{-1}$ (OH, NH); 2924–2854 $cm^{-1}$ (CH); 1735 $cm^{-1}$ (CO acid and ester) 1656–1550 $cm^{-1}$ (CO amide) ; 1037 $cm^{-1}$ (glucosidic COC).

NMR analysis:

Analysis of EPS II as such dissolved in $D_2O$ (deuterated water) showed the structure of a polysaccharide containing aliphatic chains; in addition to the presence of methylene groups, very intense signals relating to the presence of methyl and acetyl groups are observed.

Aminated sugars:

Aminated sugars were determined on EPS II hydrolyzed with the method of Z. Dische [Methods of Biochem. Anal., 2, 352–358 (1967)] which consists in deaminating the sugars with nitrous acid, destroying the excess reagent with ammonium carbamate and reacting the deaminated sugars with indole in HCl.

Other sugars were determined with the method of Dubois et al., [Anal. Chem. 28, 350–356 (1956)] using a glucose standard.

Glucose determined with the UV Test Boehringer (hexokinase, ATP, glucose-6-phosphate dehydrogenase and NADP) proved to be absent.

Esterified fatty acids [I. Stern & B. Shapiro, J. Clin. Path., 6, 158–160 (1953); sucrose dipalmitate standard (SERVA): the acid radicals esterified by reaction with hydroxyamine are transformed into hydroxamic acids which give a purple colouring with ferric chloride.

EPS II proves to consist of a heteropolysaccharide skeleton bound by an ester bond to a lipidic fraction consisting of saturated and/or unsaturated acid radicals with a length of the lipophilic chain of 10 to 18 carbon and wherein said fraction consists of about 5–20% of lipopolysaccharide.

To identify the constituents of the lipidic fraction an alkaline hydrolysis of the EPS II was carried out in order to directly obtain methyl esters of fatty acids (according to protocol Nr. 969.33 of the Association of Official Analytical Chemists ("Official Methods of Analysis of AOAC International", P. Cunnif Ed., 16th ed., Vol. II, # 41.1.28, AOAC Int. (1995)].

In practice the EPS II was treated at boiling point with methanol soda in the presence of boron trifluoride as catalyst for the formation of methyl esters of fatty acids. The esters were subsequently extracted with n-heptane and the fatty acids identified by gaschromatography/mass spectrometry.

The results showed the presence of dodecanoic acid (lauric acid) as main product, 3-hydroxy-dodecanoic acid as secondary product and smaller quantities of 2-hydroxydodecanoic, hexadecanoic (palmitic acid), octadecanoic (stearic acid) and octadecenoic (oleic acid) acids.

A comparison with Emulsan showed the following differences:

TABLE 2

| Fatty acid | EPS II | Emulsan |
|---|---|---|
| | % total fatty acids | |
| decanoic (capric) | — | 11.4 |
| dodecanoic (lauric) | 69.8 | 23.0 |
| dodecenoic | — | 2.4 |
| 2-hydroxydodecanoic | 2.6 | 10.5 |
| 3-hydroxydodecanoic | 20.3 | 39.5 |
| hexadecenoic | 2.0 | 0.7 |
| hexadecenoic | — | traces |
| octadecanoic | 0.8 | 0.3 |
| octadecenoic | 0.9 | traces |
| not identified | 3.9 | 12.0 |

Although the quantity of fatty acids may vary from sample to sample and in relation to the growth conditions, dodecanoic acid and 3-hydroxy-dodecanoic acid are always present as main products and within a range of 95 to 50% and dodecanoic acid is generally predominant with respect to 3-hydroxy-dodecanoic acid.

The characterization of the polysaccharide skeleton of EPS II was carried out by acid hydrolysis of the polymer, in an inert atmosphere, incubating at 105° C. for 4 hours. After cooling, the acid was removed under vacuum the precipitate was disrupted and extracted with ethyl ether, and then. dissolved in $D_2O$ and subjected to NMR analysis.

Figure 2:
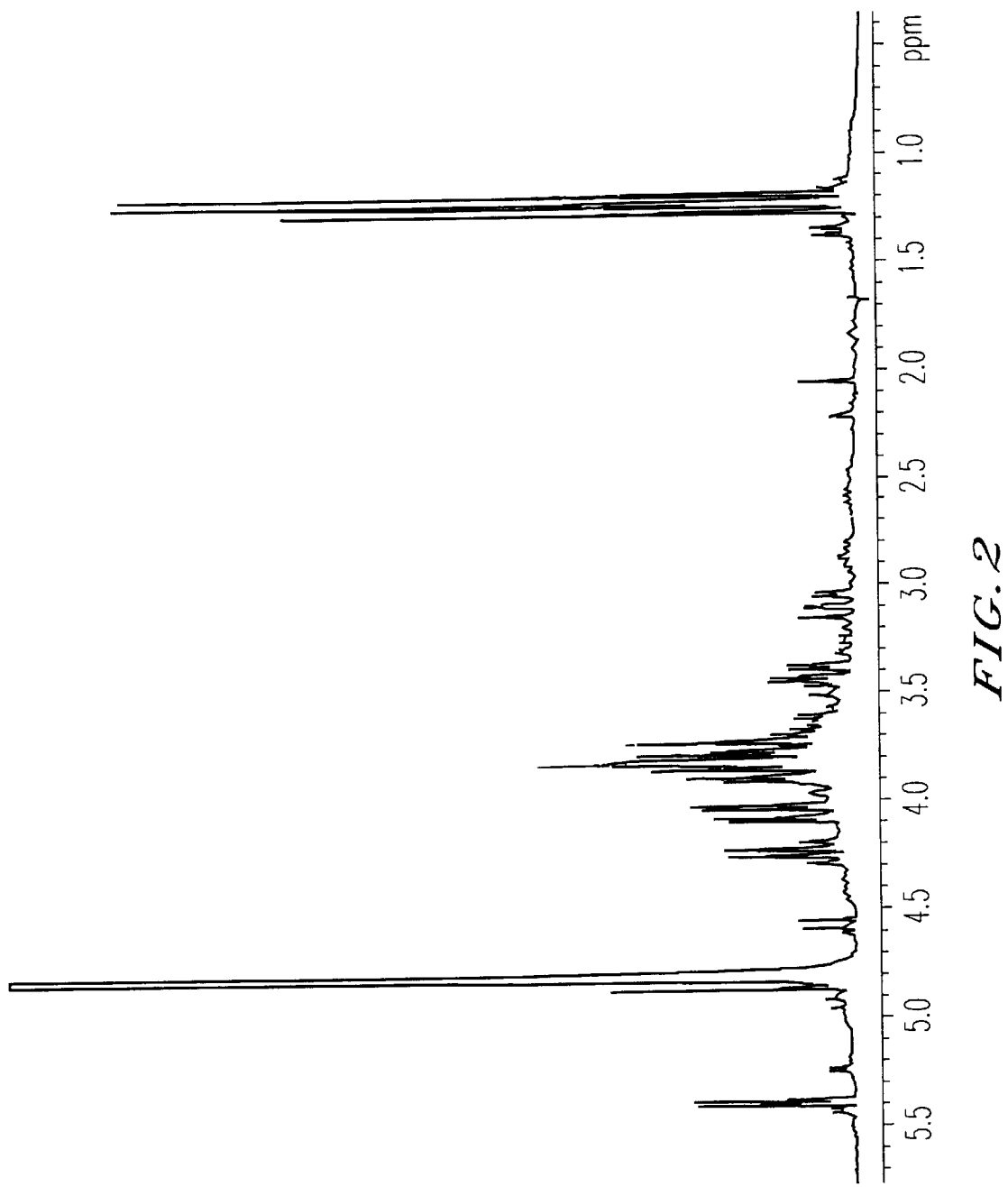
FIG. 2: NMR spectrum of EPS II hydrolyzed with HCl 5 M at 105° for 4 hours and then extracted with ether.
Figure 3:
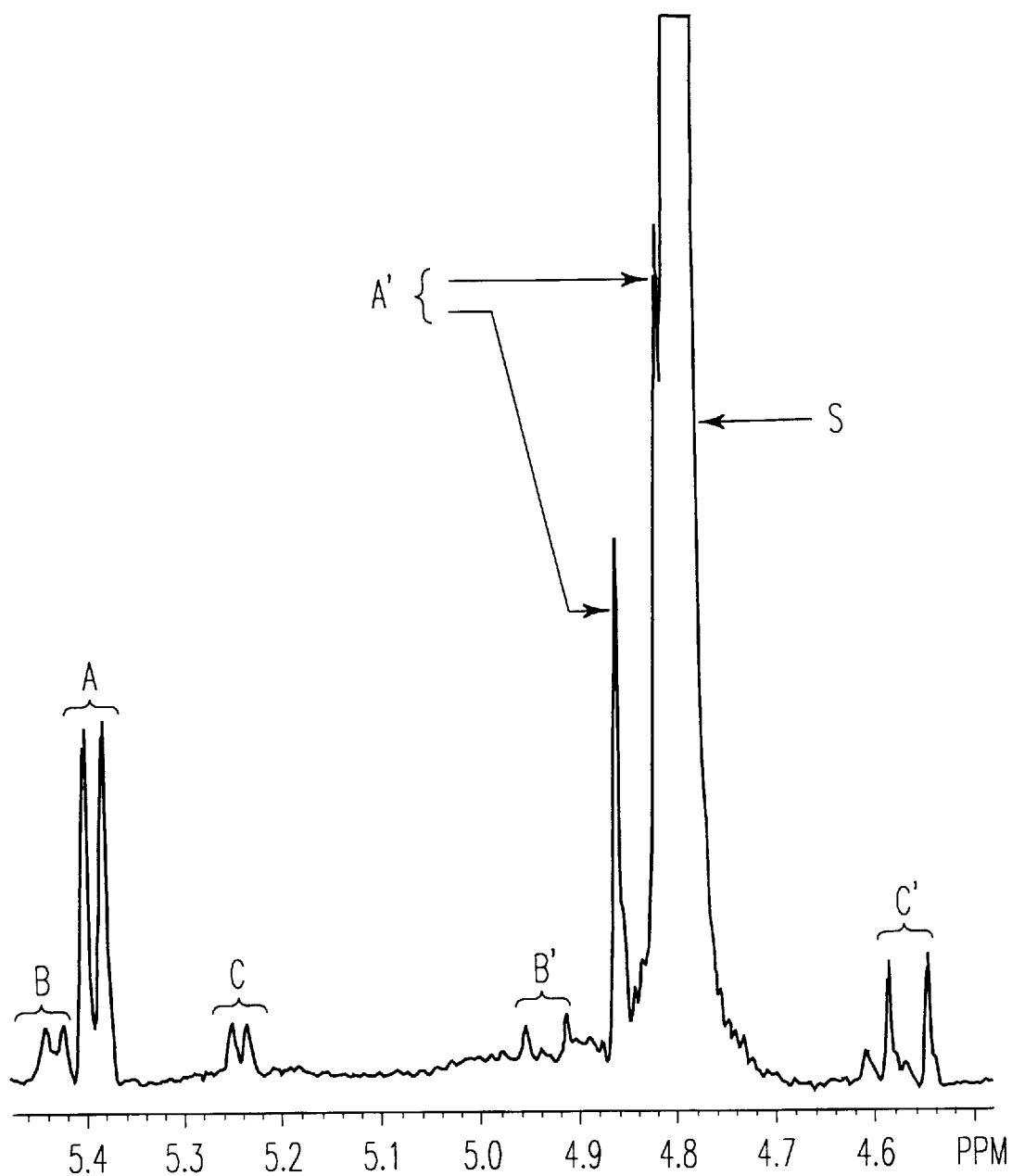
FIG. 3: Part of FIG. 2 ranging from 4.5 to 5.5 ppm. 3 carbohydrates can be observed from the three couples of doublets relating to α and β forms wherein A,A'=2-amino-2,6-dideoxyaldohexose, B,B'=glucosamine and C,C'=non-identified carbohydrate, S=solvent.

The NMR spectrum of the complete proton is indicated in FIG. 2, whereas FIG. 3 shows an enlargement of the region of the previous spectrum (FIG. 2) between 4.5 and 5.5 p.p.m., which comprises the signals of the protons relating to carbon in position 1 of monosaccharides in general.

These signals are generally double owing to the simultaneous presence in solution of α and β anomer forms of monosaccharide. The spectrum of FIG. 3 shows 3 pairs of doublets relating to 3 species of monosaccharides, one of which is predominant with respect to the other two.

To identify the monosaccharides which form the polysaccharidic skeleton of EPS II a preparative acid hydrolysis was carried out. The most suitable hydrolysis conditions were first determined by incubating aliquots of EPS II at 100° C. for various times with different concentrations of HCl. The hydrolyses were followed by determining both the aminated sugars and reducing sugars [J. T. Park & M. J. Johnson, J. Biol. Chem., 181, 149 (1949)]; the best conditions were identified in a hydrolysis with HCl 0.5 M for 6 hours.

On the basis of these results, the EPS II was dissolved in HCl 0.5 M, and under a gas seal of $N_2$, it was reflux boiled for 6 hours. The solution was cooled, concentrated under vacuum and extracted three times with equal volumes of ethyl ether. The solution was subsequently evaporated, then diluted with water and reconcentrated under vacuum; this treatment was repeated three times before drying.

The dry product was added to water and then treated according to the scheme described by R. W. Weath [Methods Enzymol., 8, 60–78 (1966)]. The hydrolyzed product was charged onto a column of strong cationic resin in the form of H+ and the column was subsequently eluated with water until the pH of the eluate had returned to neutrality.

The fraction not withheld by the resin and consisting of neutral sugars and/or acids was only partially characterized: a positive reaction was found for the Dubois test, negative for the aminated sugar test, positive for uronic acids [T. Bitter & H. H. Muir, Anal. Biochem., 4, 330–334 (1962)].

The column, onto which the amino sugars had been fixed, was isocratically eluated with HCl 0.3 M. The fractions collected were analyzed for the reducing sugars and two chromatographic peaks were observed. The fractions relating to the peaks were joined, dried and added to water several times to remove the Hcl and were then lyophilized and subjected to NMR analysis.

Figure 4:
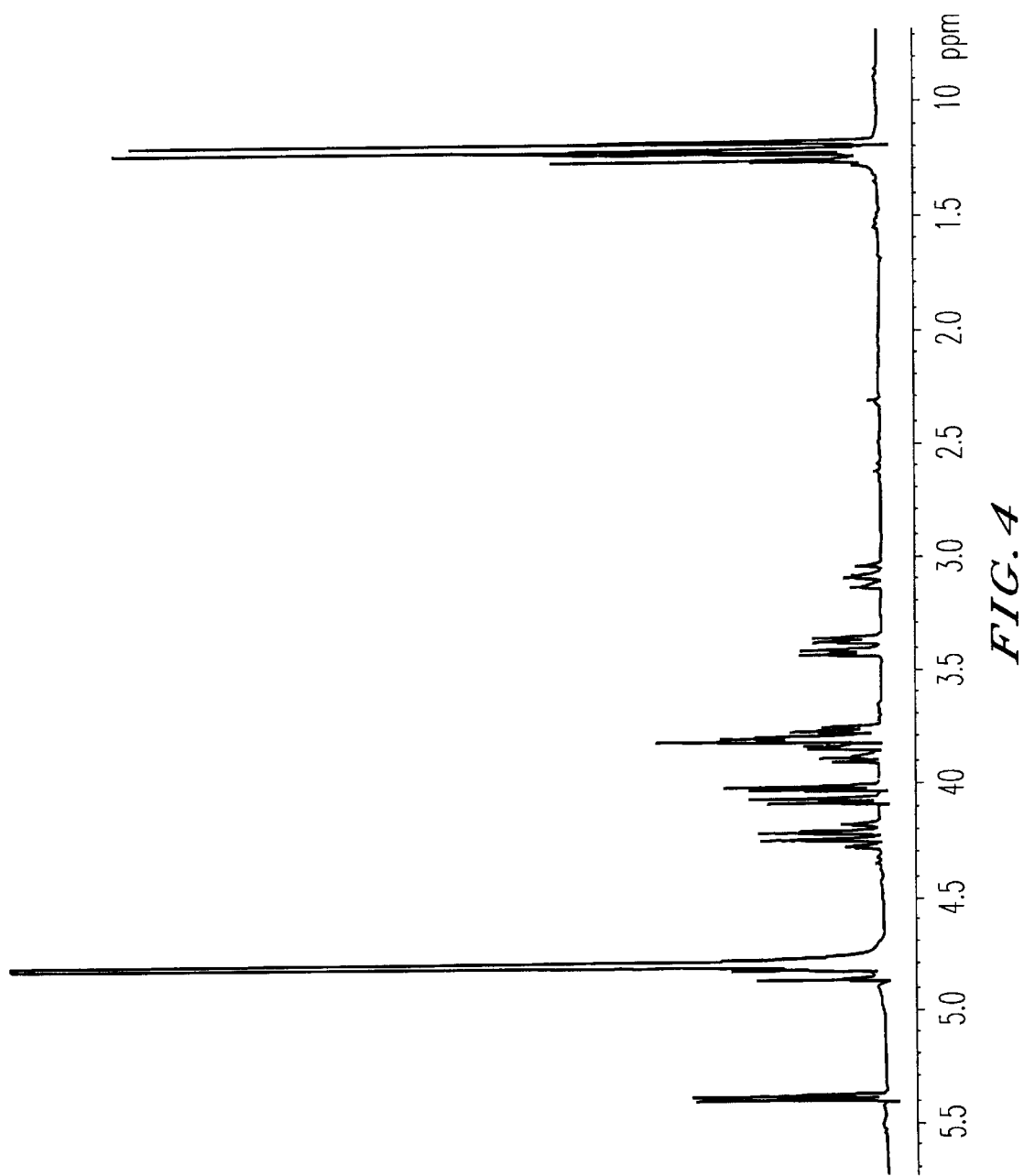
FIG. 4: NMR spectrum of the proton of 2-amino-2,6-dideoxyaldohexose which represents the main constituent of the polysaccharide skeleton of EPS II.

The first peak was identified as glucosamine: The NMR spectrum of the proton was equal to that of a commercial sample of glucosamine.HCl (Fluka). The spectrum of the second peak (FIG. 4) is consistent with that of an aminohexose with a methyl in position 6 (rather than —$CH_2OH$); more specifically, the compound proves to be a 2-amino-2, 6-dideoxyaldohexose and represents about 70–80% of the polysaccharidic skeleton.

The presence of the amine group in position 2 was confirmed by the Rondle-Morgan reaction which generated a chromophore with maximum absorption at 530 nm [C. J. M. Rondle & W. T. J. Morgan, Biochem. J., 61, 586 (1955); N. Suzuki, Biochem. Biophys. Acta, 177, 371–373 (1969)].

In conclusion, the experimental results indicate that the lipopolysaccharide comprises a heteropolysaccharidic chain consisting of 70–80% of a 2-amino-2,6-dideoxyaldohexose, 5–10% of glucosamine and 15–20% of one or more nonaminated sugars. The amine groups prove to be totally or almost totally acetylated.

The main differences with the bioemulsifying agents of the known art are indicated in table 3 below.

TABLE 3

| Monosaccharide | EPS | Emulsan | BSF217 |
|---|---|---|---|
| Glucose | absent | 0–5.2% | 31% |
| Mannose | n.d. | absent | 15.5% |
| Galactose | n.d. | absent | 22.5% |
| D-galactosamine | absent | 20–30% | absent |
| Glucosamine | 5–10% | absent | absent |
| 2-amino-2,6-dideoxyhexose | 70–80% | absent | absent |
| 2-amino-2-deoxyhexuronic ac. | absent | 33% | absent |
| Uronic acids | probable | absent | 10–18% |

The functional characterization of the biosurfactant of the present invention relates mainly to the stimulus for biodegradation of crude oil in sea water and adhesion stimulation of the microbic cells to the surface of hydrocarbons.

For this purpose two types of experiments were carried out in which the degradation was recorded of a crude oil in sea water on the part of hydrocarbonclastic microbic flora adapted for growth on hydrocarbons and also autochthon microbic flora of sea water.

The experimentation was carried out by incubating the above microbic flora with crude oil in the presence of and without the biosurfactant produced by A. calcoaceticus ER-96 and also comparing the effect induced by this biosurfactant with that of a commercial dispersing agent.

Both raw EPS and EPS were used with the aim of separating the effects due to nutrient substances possibly present in the fermentation broth from that relating to the biosurfactant, with the same results.

To measure the biodegradation of the crude oil, the cultures, after various incubation times, were mixed with freon-113®, centrifugated, and the residual hydrocarbons were determined in the organic extracts by spectrophotometry in infra-red according to the EPA 418.1 method [in "Methods for Chemical Analysis of Water and Wastes", J. F. Kopp & G. D. McKee Eds., Report Nr. EPA-600/4-79-020 (1983)].

The results showed that a microbic flora adapted for growth on n-hexadecane had degraded in the presence of raw EPS, after 14 days of incubation, 75% of the initial crude oil. This value proved to be about 6 times greater that that without EPS and about 3 times greater than that obtained with the commercial dispersing agent.

It was also observed that the biodegradation in the presence of EPS is doubled and also increases the biomass by 5 orders (from $1.10^4$ to $3.10^9$) which in the control without EPS is increased only a hundred times.

In addition gaschromatographic analysis of the variations in the ratios between n-heptadecane and pristane and between n-octadecane and phytane showed that also these indexes in the presence of EPS vary much more than in the controls without EPS.

In conclusion, the biosurfactant of the present invention stimulates the biodegradation of hydrocarbons in sea water on the part of both hydrocarbonclastic microbic flora adapted for growth on hydrocarbons and autochthone microbic flora. It is important to remember that in this respect Emulsan has an inhibiting effect.

To determine the capacity of EPS to promote adhesion of hydrocarbonclastic microorganisms to hydrocarbons, the method adopted for Emulsan was used [E. Rosenberg et al. [Infect. Immun., 39, 1024–1028, 1983]. The method consists in wriggling a microbic suspension with a certain Quantity of hydrocarbons and measuring the reductionn in turbidity of the microbic suspension due to adhesion.

It was found that, in direct contrast with what occurs with Emulsan, EPS promotes adhesion of the bacterial cells to the water/hydrocarbon interface.

In fact, using both a pure culture of Arthrobacter sp. and the total heterotroph flora present in sea water, the adhesion was from 2 to 4 times greater with EPS than the control without EPS.

In conclusion, in addition to the differences in structure of the two biosurfactants, there is experimental evidence that there is different functional behaviour of EPS with respect to Emulsan: 1) the biodegradation of hydrocarbons in water which Emulsan inhibits and which EPS seems to promote and 2) adhesion to the water/oil interface which increases instead of decreasing with the biosurfactant of the present invention.

The biosurfactant of the present invention is therefore particularly suitable for the treatment of "oil spills" in both the sea and internal water.

The production of the biosurfactant is obtained by cultivating the strain *A. calcoaceticus* ER-96 in a culture medium containing carbon sources, nitrogen, phosphorous and sulfur, and mineral salts.

Assimilable carbon sources comprise for example ethanol, sodium, palmitate, oleic acid, soybean oil, etc.

These sources are generally used at a concentration ranging from 0.2 to 5% with respect to half the culture, and preferably from 1 to 3%.

Nitrogen sources can be selected, for example, from mineral ammonium salts, such as ammonium nitrate, ammonium sulfate, ammonium-chloride, ammonium bicarbonate or materials containing organic or inorganic nitrogen such as peptone, yeast extract or meat extract, and also ammonia can be used.

Phosphorous sources comprise dibasic or monobasic potassium phosphate, sodium phosphate, ammonium phosphate, etc.

The following cations and anions are equally suitable for the purposes of the present invention: potassium, sodium, magnesium, iron, calcium, manganese, cobalt, copper, zinc, molibden, phosphates, sulfates and chlorides. Concentrations ranging from 1 to 100 mM are generally used.

The fermentation is carried out in a stirred and extremely aerated medium, at a temperature ranging from 25 to 37° C., preferably between 28 and 32° C.

Sterile compressed air is circulated in the fermentation medium in a quantity varying from 0.2 to 1 vol/vol/minute.

The pH of the fermentation medium is maintained within values ranging from 6.5 to 7.5 and preferably between 6.8 and 7.2. The pH regulation can be carried out, for example, by the addition of a basic aqueous solution such as an aqueous solution of ammonia, potassium hydroxide, sodium hydroxide.

It is preferable to maintain the pH at the desired value using ammonium hydroxide 10 M.

The foam which is formed in the fermentation can be controlled by the addition of a suitable antifoam agent selected from those available on the market such as for example polypropyleneglycol, or with mechanical devices.

The fermentation process can be carried out in batch, in fed batch, or in continuous.

At the end of the fermentation the biosurfactant can be isolated and purified using one of the known techniques. Alternatively the fermentation broth as such or without cells, can be used directly.

The determination of the concentration of lipopolysaccharide in the culture broth during and at the end of the fermentations of the producer strain can be carried out in two ways: the first consists in measuring the emulsifying capacity of the fermentation broth and obtaining the concentration of Enispol by means of a calibration curve; the second consists in determining the aminated sugars and also in this case obtaining the concentration of EPS by means of a calibration curve.

The following examples have the sole purpose of describing the present invention in greater detail and should not be considered as limiting the scope of the invention in any way.

EXAMPLE 1

Isolation of *Acinetobacter calcoaceticus* ER-96

150 g portions of a mixture of polluted soils were placed, to favour the revivification of the biomass, in 2000 ml flasks containing 500 ml of Bushnell-Haas medium (BHB) with the following composition per liter of distilled water:

$KH_2PO_4$ 1 g; $K_2HPO_4$ 1 g; $NH_4NO_3$ 1 g; $MgSO_4 \cdot 7H_2O$ 0.2 g; $CaCl_2 \cdot 2H_2O$ 0.02 g; $FeCl_3$ 0.05 g; pH 7.0 with NaOH 0.1N; 100 mg/l of yeast extract.

The flasks were incubated for 8 hours at 22° C. in an orbital stirrer at 200 revs/min.

Aliquots of 10 ml of the culture broths were used as inocula of a series of 500 ml flasks each containing 100 ml of Buffered Mineral Medium (BMM) modified according to Mills et al. [Can. J. Microbiol., 24, 552–557 (1978)] containing per litre of distilled water: NaCl 5 g; $MgSO_4 \cdot 7H_2O$ 1 g, KCl 0.7 g, $KH_2PO_4$ 2 g, $Na_2HPO_4$ 3 g, $NH_4NO_3$ 1 g, pH 7.2 and 1% of a hydrocarbon carbon source selected from AGIP® fuel oil, "Forties" crude oil, and Carlo Erba® vaseline oil. The flasks were incubated at 22° C., on an orbital stirrer at 200 revs/min, for 10 days.

The culture broths were then used to carry out a series of three subcultures for each of the carbon sources used.

The various culture broths were inoculated in 50 ml flasks each containing 20 ml of BMM and 0.1 ml of the carbon source, subsequently incubating at 22° C. on an orbital stirrer at 200 revs/min for 5 days.

The isolation of the single microbic phenotypes present in the enriched culture broths was carried out by plating on "LAB-LEMCO Broth medium (OXOID) agarized at 2%. The plates were incubated at 22° C. for 48 hours.

Among all the colonies developed those apparently differing from each other in morphological and/or pigmentation characteristics were selected.

These colonies were isolated and inoculated in 50 ml flasks containing 20 ml of BHB and 1% of "light arabian" crude oil. The flasks were incubated for 7 days at 22° C. on an orbital incubator at 200 revs/min.

Strips of the single pure cultures thus obtained were shuffled on plates of agarized BHB medium at 2%.

The carbon source was administered in gaseous phase, placing a disk of filter paper soaked with a mixture of crude oil/vaseline oil/gas oil by autotraction (50:40:10), in the lid of the plate. The plates were incubated for 7 days at 22° C. in an oven.

The colonies removed from each plate were suspended in BHB at various dilutions and used for the "crack test" [Krigsvoll et al., "Microbial emulsification of crude oil" in Proceedings of the 5th European Congress in Biotechnology, Vol. I, pages 221–224, Copenhagen, July 1990].

For this purpose polystyrene plates with 24 test-holes were used, introducing 1 ml of microbic suspension in each test-hole and carefully topping up with 0.025 ml of crude oil. The test-holes were immediately examined under the microscope (10 X) to observe the fracture of the oily meniscus which indicates the presence of surfactants.

Among the various strains which gave a positive signal, only one proved to be capable of producing a biosurfactant with a high emulsifying capacity. This strain was indicated with the abbreviation ER-96 and was subsequently identified as *Acinetobacter calcoaceticus*.

EXAMPLE 2

Production of EPS in Batch Fermentation

Lyophilized cells of *A. calcoaceticus* ER-96 were revitalized in "Lab-Lemco" Broth medium (OXOID CM 15) and a 250 ml flask containing 50 ml of culture medium (T1) containing per liter: ethanol 10 g, $KH_2PO_4$ 10 g, $NH_4Cl$ 4.0 g, $MgSO_4·7H_2O$ 0.5 g, $CaCl_2$ 2.08 mg, $CoCl_2·6H_2O$ 2.08 mg, $MnCl_2·4H_2O$ 1.73 mg, $Na_2MoO_4$ 2.12 mg, $MnSO_4·H_2O$ 1.49 mg, $ZnSO_4·7H_2O$ 2.52 mg, $FeSO_4·7H_2O$ 2.43 mg, pH adjusted to 7.4 with NaOH, was inoculated with this culture (5%).

The flask was incubated on an orbital stirrer at 180 revs/min, at 30° C. for 48 hours and then used to inoculate a 2 l flask, equipped with breakwaters, containing 500 ml of T1 medium.

The culture was prolonged for 48 hours under the above conditions and was subsequently used to inoculate (5%) a 14 l Chemap® fermenter, with breakwaters, containing 10 l of T2 culture broth having the same composition as the T1 medium, but with 7 g/l of $KH_2PO_4$, 10 g/l of $NH_4Cl$ and 1 g/l of $MgSO_4·7H_2O$.

The fermentation was carried out with an aeration of 0.5 l/l per minute, at 30° C., stirring with 2 turbines at 700 revs/min.

The pH was automatically corrected to 7 with NaOH and the foaming controlled with Polypropyleneglycol (PPG 2000).

After 22 hours, the fermentation broth was centrifuged to remove the cells and the surnatant (which forms raw EPS) was lyophilized. 700 mg/l of product and 3.7 g/l (dry weight) of biomass were obtained.

EXAMPLE 3

The fermentation was carried out under the same operating conditions described in example 2, but using $NH_4OH$ 10 M to correct the pH to 7.

1.3 g/l of product and 4.2 g/l (dry weight) of biomass were obtained.

EXAMPLE 4

Production of EPS from Ethanol with Fed Batch Fermentation

*A. calcoaceticus* ER-96 was cultured under the same operating conditions as example 3. When the optical density at 660 nm of the culture broth reached a value of 4, a solution of aqueous ethanol at 47.5% was added to the fermentation broth with such a flow-rate as to impose a duplication time of 24 hours of the cells. After 83 hours of culture, the fermentation was interrupted. The yield of EPS was 6.7 g/l, that of the cells 13 g/l (dry weight).

EXAMPLE 5

*A. calcoaceticus* ER-96 was cultured with the same procedure as example 4, except that the foaming was mechanically controlled with the use of Fundafoam®(Chemap) foam-breaker; in addition, the initial concentration of ethanol was 5 ml/l. After 14 hours, when the optical density at 660 nm of the culture broth had reached a value of 4.5, the addition of ethanol was started, in such a quantity as to impose a duplication time of 16 hours. The fermentation was prolonged for 90 hours. 20 g/l of EPS and 21 g/l of biomass were obtained.

EXAMPLE 6

Production of EPS from Oleic Acid

*A. Calcoaceticus* ER-96 was cultured under the same operating conditions as example 4, but using oleic acid instead of ethanol as single carbon source. After 83 hours the yield of EPS was 7.5 g/l, that of the cells 24.8 g/l (dry weight).

EXAMPLE 7

Production of EPS from Soybean Oil

Cells of *A. calcoaceticus* ER-96 were cultured adopting the same procedure as example 6, but using soybean oil instead of oleic acid as single carbon source. After 72 hours of fermentation the yield of EPS was 15 g/l, that of the cells 20 g/l (dry weight).

EXAMPLE 8

Preparation of EPS

Cells of *A. calcoaceticus* ER-96 were cultured in a 14 liter Chemap® fermenter containing 10 l of T2 medium to which 20 g/l of ethanol had been added. Further ethanol was added at various times as required and the pH was maintained at 7 with ammonia.

The fermentation was carried out with aeration (0.5 l/l per minute) for 70 hours, at 30° C. At the end the culture was cooled to room temperature and the cells removed by centrifugation (Alfa-Laval® LAPX 202).

Ammonium sulfate (166 g/l) was added to the surnatant (10.4 l) which was left under stirring for a night and then centrifuged (13,000×$g_{max}$; Sorvall-DuPont® RC-5B).

Ammonium sulfate (57 g/l) was added to the limpid surnatant and after 4 hours of stirring the precipitate was recovered by centrifugation, dissolved with a minimum quantity of water, dialyzed against water and lyophilized.

38.5 g of EPS were obtained with a specific emulsifying capacity of 93 UE/mg.

The emulsifying capacity was determined with a modification of the method of Gutnick et al. [EPA 16546]. In practice, 3.25 ml of a solution of EPS in a buffer of tris-hydroxymethylaminomethane (Tris-HCl) 50 mM brought to pH 7.2 with HCl and containing $MgSO_4$ 10 nM were introduced into a boronsilicate 25×80 mm, glass test-tube, with a screw top and teflon seal and 50 µl of a mixture of n-hexadecane and 2-methylnaphthalene (1:1; v/v) were added. The mixture was stirred at 800 strokes/min with a vertical shake stirrer having an amplitude of 10 mm ("Agitest" Bioblock) for 5 minutes, then the whole contents of the test-tube were poured into a glass cuvette and the absorbance at 620 nm was determined. The quantity of biosurfactant that under the standard conditions described above gives an optical density of 1 is defined with Eniricerche emulsifying capacity Units (1 UE). The specific emulsifying capacity was consequently defined as the emulsifying capacity of 1 mg of product.

EPS proved to consist of about 22% of proteins (Bio-Rad Protein Assay Kit), about 67% of a lipopolysaccharide and the remaining percentage of metallic ions, essentially magnesium and sodium.

EXAMPLE 9

Preparation of EPS II

A fermentation of *A. calcoaceticus* ER-96 was carried out under the same conditions as example 4. At the end, 1660 g of ammonium sulfate were added to 10 l of this culture broth. After a night at 4° C. under stirring, the suspension was centrifuged (13,000×$g_{max}$) and 434 g of ammonium sulfate were added to the resulting surnatant (7.6 liters).

After a night at 4° C., the suspension was centrifuged and the precipitate was dissolved in 2 l of water and concentrated by passage through an ultrafiltration spiral membrane with a cut-off of 10,000 Daltons (Amicon S1Y1O) up to a volume of 400 ml.

The solution was then diluted again with water up to 2 liters and reconcentrated to 400 ml and this treatment was repeated 10 times. The final retention (1 l), to which 1 l of Tris-HCl 0.1 M buffer containing $MgCl_2$ 10 mM pH 7.2 and 500 units of Benzonase Grade I (Benzon Nuclease®, Merck) had been added, was maintained at 25° C. for 3 hours to destroy any DNA and RNA possibly present.

The solution thus obtained was concentrated to 1 liter, 1 l of Tris-HCl 50 mM buffer containing $EDTANa_2$, 0.2 M and 1,4-dithiothreitol 2 mM, pH 8 was added and the whole mixture was incubated in the presence of 32 mg of Papain (Calbiochem) at 25° C. for a night.

The mixture reduced to 1 litre was heated to 70° C. and then an equal volume of phenol redistilled and preheated to 70° C. was added, according to the method of O. Westphal & K. Jann ("Methods in Carbohydrate Chemistry" arranged by R. L. Whistler, Vol. V, pages 83–91, Academic Press, Inc., New York, 1965). After 15 minutes at 70° C. under vigorous stirring, the mixture was cooled to room temperature and the emulsion formed was separated by centrifugation at 23,000×$g_{max}$.

The phenolic phase was extracted three times with an equal volume of water and the aqueous extracts were joined and, after being extracted three times with an equal volume of ether, were concentrated with the membrane to 500 ml. After the addition of 500 ml of $EDTANa_2$ 0.1 M pH 8, the solution was reconcentrated to 500 ml and this treatment was repeated 6 times.

Subsequently, using the same procedure, 10 liters of $H_2O$ (20 times), 10 liters of NaCl 0.1 M (20 times), 10 litres of HCl 50 mM (20 times) and 10 litres of $H_2O$ (20 times) were added and eluated. The resulting solution was lyophilized obtaining 6.9 g of EPS II with a specific emulsifying capacity of 48 UE/mg.

EXAMPLE 10

Physico-chemical Characterization of EPS II

The EPS II obtained as described in example 9 was analyzed and the following characteristics were determined:

Drying loss (70° C.; under vacuum; 16 hours) : 3.7% (w/w).

Elemental analysis (%): C=44.5; H=7.33; N=4.99; O=40.6; S=0.

Ash (900° C.): 3.6% (w/w).

Proteins [Bio-Rad Protein Assay; M. Bradford, Anal. Biochem., 72 248 (1976), bovine y-globulin standard]: 58.6 mg/g.

Metals (atomic or emission absorption spectroscopy): Na=7800; Ca<10; Mg=60; Mn=1; Cu=3; Co<10; Ni<2; Fe<10 (in p.p.m.).

Infra-red spectrum (FT-IR).

With reference to FIG. 1: 3417.5 $cm^{-1}$ (OH, NH); 2924–2853 $cm^{-1}$ (CH) ; 1735 $cm^{-1}$ (CO acid and ester) 1655–1554 $cm^{-1}$ (CO amide); 1038 $cm^{-1}$ (glucosidic COC).

NMR spectra.

The proton and $^{13}C$ spectra of EPS II dissolved in $D_2O$ were recorded. The spectra proved to be consistent with the structure of a polysaccharide containing aliphatic chains, but as well as the presence of methylene groups very intense signals relating to the presence of methyl and acetyl groups were observed.

Aminated sugars:

The EPS II was hydrolyzed in HCl 5 M, at 100° C. for 30 minutes and neutralized. The aminated sugars were then determined with the method of Z. Dische [Methods of Biochem. Anal., 2, 352–358 (1967)] which consists in deaminating the sugars with nitrous acid, destroying the excess reagent with ammonium carbamate and reacting the deaminated sugars with indole in HCl.

Using N-acetylglucosamine as standard a value of 604 mg/g was found.

Other sugars [Dubois et al., Anal. Chem. 28, 350–356 (1956); glucose standard]: 190 mg/g.

Glucose (UV Test Boehringer: hexokinase, ATP, glucose-6-phosphate dehydrogenase and NADP): absent.

Molecular weight: this was determined with HPLC-SEC (Size exclusion chromatography) analysis on Waters Styragel $10^6$, Styragel $10^5$ and Styragel $10^4$ columns, using dimethylsulfoxide as mobile phase and pullulanes as standards (Hayashibara Biochemical Laboratories Inc., Japan). A value of 1,556,400 daltons was found.

Esterified fatty acids [I. Stern & B. Shapiro, J. Clin. Path., 6, 158–160 (1953); sucrose dipalmitate as standard (SERVA)]: the acid radicals esterified by reaction with hydroxyamine are transformed into hydroxyamic acids which give a purple colouring with ferric chloride; 1.15 meq/g was found.

Assuming an average molecular weight of 182,32 (lauryl radical) a content of fatty acids of 209.7 mg/g was calculated.

EXAMPLE 11

Characterization of the lipopolysaccharide

To characterize the lipidic fraction of the biosurfactant protocol Nr. 969.33 of the Association of Official Analytical Chemists was used ["Official Methods of Analysis of AOAC International", P. Cunnif Ed., 16th ed., Vol. II, #41.1.28, AOAC Int. (1995)].

In practice the EPS II was treated at boiling point with methanol soda in the presence of boron trifluoride as catalyst for the formation of the methyl esters of fatty acids.

The esters were then extracted in n-heptane and the fatty acids were identified by gaschromatography/mass spectrometry.

Operating as described above the following products were identified:

dodecanoic acid (lauric acid) as main product;

3-hydroxy-dodecanoic acid as secondary product and smaller quantities of 2-hydroxydodecanoic, hexadecanoic (palmitic acid), octadecanoic (stearic acid) and octadecenoic (oleic acid) acids.

The characterization of the polysaccharidic skeleton of EPS II was carried out by acid hydrolysis of the polymer.

80 mg of EPS II were dissolved in 8 ml of HCl 5 M and incubated, in an inert atmosphere, for 4 hours at 105° C. After cooling to room temperature the HCl was removed under vacuum.

The resulting precipitate was disrupted and extracted with ethyl ether, then dissolved in $D_2O$ and subjected to NMR analysis.

The NMR spectrum of the complete proton is indicated in FIG. 2.

FIG. 3 shows an enlargement of the region of the previous spectrum between 4.5 and 5.5 p.p.m., which comprises the signals of the protons relating to carbon in position 1 of monosaccharides in general.

These signals are generally double due to the simultaneous presence in solution of $\alpha$ and $\beta$ anomer forms of monosaccharide. The spectrum of FIG. 3 shows 3 pairs of doublets relating to 3 species of monosaccharides in a ratio of 7:2:1.

To identify the monosaccharides forming the polysaccharidic fraction of EPS II, a preparative acid hydrolysis was carried out.

First of all, the most suitable hydrolysis conditions were determined by incubating aliquots of EPS II at 100° C. for various times with different concentrations of HCl. The hydrolyses were following by determining both the aminated sugars and the reducing sugars [J. T. Park & M. J. Johnson, J. Biol. Chem., 181, 149 (1949)]. The best conditions were identified in a hydrolysis with HCl 0.5 M for 6 hours.

On the basis of these results 500 mg of EPS II were dissolved in 500 ml of HCl 0.5 M and reflux boiled for 6 hours, under a gas seal of $N_2$.

The solution was then cooled, concentrated to 50 ml under vacuum and extracted three times with equal volumes of ethyl ether.

The resulting solution was evaporated to 10 ml, diluted to 100 ml with water and reconcentrated to 10 ml under vacuum. This treatment was repeated three times before drying by rotavapor.

The dry product was added to 200 ml of $H_2O$ and then treated according to the scheme described by R. W. Weath [Methods Enzymol., 8, 60–78 (1966)].

The hydrolyzed product was charged onto a column (1.2 cm d.i.×50 cm h) of Dowex® 50 X-4, 200–400 mesh strong cationic resin, in the form of $H^+$, and the column was subsequently eluated with water until the pH of the eluate was neutral.

The fraction present in the eluate, not withheld by the resin, consisted of neutral sugars and/or acids and represented about 20% of the total. Its characterization showed a positive reaction for the Dubois test, negative for the aminated sugar test and positive for uronic acids [T. Bitter & H.H. Muir, Anal. Biochem., 4, 330–334 (1962)].

The column, onto which the aminosugars had been fixed, was isocratically eluated with HCl 0.3 M. The fractions collected were analyzed for the reducing sugars and two chromatographic peaks were observed.

The fractions relating to these peaks were joined, dried and added to water several times to remove the HCl. The fractions were then lyophilized and subjected to NMR analysis.

The first peak, which was about 10% of the total, was identified as glucosamine; the NMR spectrum of the proton was equal to that of a commercial sample of glucosamine-.HCl (Fluka). The spectrum of the second peak (FIG. 4) was consistent with that of an aminohexose with a methyl in position 6. More specifically, the compound proved to be a 2-amino-2,6-dideoxyaldohexose.

The presence of the amine group in position 2 was also confirmed by the Rondle-Morgan reaction which generated a chromophore with maximum absorption at 530 nm [C. J. M. Rondle & W. T. J. Morgan, Biochem. J., 61, 586 (1955); N. Suzuki, Biochem. Biophys. Acta, 177, 371–373 (1969)].

EXAMPLE 12

Biodegradation of Crude Oil in Sea Water with EPS

Aliquots (7.5 mg) of raw EPS, prepared by lyophilizing a culture broth obtained as described in example 4, after depriving it of cells by centrifugation, were introduced into a series of 250 ml flasks each containing 50 ml of sea water with a total heterotroph bacterial charge of $1.1 \cdot 10^3$ UFC (Colony Forming Units)/ml and a content of nitrogen and phosphorous of 4 and 0.9 ppm respectively.

150 mg of "Belahim blend" crude oil, of which the most volatile fraction had been previously removed by heating to 80° C. for 20 hours, were then introduced into the flasks.

Controls without EPS and a second series of flasks containing a commercial dispersing agent used by the Italian port authorities for treating oil spills in the sea, were prepared parallelly.

The flasks were incubated under aerobic conditions on an orbital stirrer at 100 revs/min at 22° C., taking test samples at zero time and at different time intervals to determine the content of biomass and hydrocarbons. The biomass was determined by means of a count of the total heterotroph bacteria effected on agarized culture medium with soybean triptone-peptone (Oxoid, CM 131). The hydrocarbons were dosed by extracting each single flask with 1,2-trichloro-1, 2,2-trifluoroethane (Freon®-113), measuring the extinction at 2930 cm$^{-1}$, corresponding to the maximum absorption, and obtaining the concentration of hydrocarbons by means of a calibration curve formed with a standard consisting of n-hexadecane/iso-octane/chlorobenzene in a volumetric ratio 15/15/10.

The results are indicated in table 4. The quantity of residual hydrocarbons is expressed in percentage with respect to the quantity present at zero time.

TABLE 4

| Time (hrs) | Degraded hydrocarbons (%) | | | Biomass (UFC) | | |
|---|---|---|---|---|---|---|
| | Control without dispersers | EPS | Commercial disperser | Control without dispersers | EPS | Commercial disperser |
| 0 | 0 | 0 | 0 | 1.1 × 10³ | 1.1 × 10³ | 1.1 × 10³ |
| 7 | 12.2 | 52.6 | 19.4 | n.d. | n.d | n.d |
| 14 | 12.5 | 73.5 | 23.5 | 1.4 × 10³ | 2.4 × 10⁵ | 1.5 × 10⁵ |

*n.d.= not determined.

The values indicated in the table show that the degradation with EPS after 14 days is 5.9 time higher than the control and 3.1 times higher with respect to the commercial dispersing agent.

EXAMPLE 13

Biodegradation of Crude Oil with ESP

To separate the effects due to nutrient substances possibly present in the fermentation broth from that relating to the biosurfactant, EPS prepared as described in example 8 was used.

In this experiment different quantities of EPS were used, from 0.75 to 7.5 mg/50 ml of sea water with a total heterotroph bacterial charge of $1·10^4$ U.F.C./ml to which 150 mg of crude oil had been added. After 45 days of incubation the following parameters were determined: the biomass, the quantity of degraded crude oil and the ratios, measured with gaschromatographic analysis (Supelco SPB1 capillary column) of the extract in Freon, between: (a) the quantities of n-heptadecane (n-$C_{17}$) and pristane and (b) the quantities of n-octadecane (n-$C_{18}$) and phytane. These ratios are generally considered important biodegradation indexes [P. Sveum et al., in "Hydrocarbon bioremediation" under the care of R. H. Hinchee et al., Lewis Publisher, Boca Raton; pages 163–174 (1994)]. 7 flasks for each of the following mixtures were prepared:

1) sea water (50 ml)+oil (150 mg)
2) sea water (50 ml)+oil (150 mg)+EPS (0.75 mg)
3) sea water (50 ml)+oil (150 mg)+EPS (3.75 mg)
4) sea water (50 ml+oil (150 mg)+EPS (7.50 mg)

The results are shown in tables 5–7:

TABLE 5

| Time | Biodegraded petroleum (%) | | | |
|---|---|---|---|---|
| | Samples | | | |
| (days) | 1 | 2 | 3 | 4 |
| 7 | 16.1 | 10.2 | 10.9 | 17.1 |
| 14 | 16.4 | 21.8 | 18.3 | 21.5 |
| 21 | 19.0 | 23.7 | 16.3 | 27.8 |

TABLE 5-continued

| Time | Biodegraded petroleum (%) | | | |
|---|---|---|---|---|
| | Samples | | | |
| (days) | 1 | 2 | 3 | 4 |
| 28 | 19.8 | 21.6 | 20.7 | 31.9 |
| 35 | 19.7 | 20.2 | 25.7 | 30.4 |
| 45 | 17.8 | 27.3 | 29.0 | 32.0 |

TABLE 6

| | Ratios n-$C_{17}$/Pristane and n-$C_{18}$/Phytane | | | | | | | |
|---|---|---|---|---|---|---|---|---|
| | Samples | | | | | | | |
| | 1 | | 2 | | 3 | | 4 | |
| Time (days) | C17/P | C18/Ph | C17/P | C18/Ph | C17/P | C18/Ph | C17/P | C18/Ph |
| 0 | 2.41 | 1.70 | 2.43 | 1.70 | 2.40 | 1.73 | 2.46 | 1.70 |
| 7 | 2.41 | 1.65 | 2.42 | 1.66 | 2.35 | 1.68 | 2.43 | 1.68 |
| 14 | 2.38 | 1.70 | 2.41 | 1.66 | 2.28 | 1.57 | 2.41 | 1.61 |
| 21 | 2.38 | 1.70 | 2.40 | 1.70 | 2.32 | 1.57 | 2.12 | 1.52 |
| 28 | 2.37 | 1.70 | 2.25 | 1.62 | 2.29 | 1.61 | 2.17 | 1.57 |
| 35 | 2.34 | 1.63 | 2.23 | 1.52 | 2.19 | 1.47 | 2.17 | 1.52 |
| 45 | 2.34 | 1.63 | 1.99 | 1.38 | 1.91 | 1.35 | 2.00 | 1.49 |

TABLE 7

| Time | Microbic count (total heterotroph bacteria, UFC/ml) | | | |
|---|---|---|---|---|
| | Samples | | | |
| (days) | 1 | 2 | 3 | 4 |
| 0 | 1.0 × 10⁴ | 1.0 × 10⁴ | 1.0 × 10⁴ | 1.0 × 10⁴ |
| 7 | 3.7 × 10⁵ | 3.2 × 10⁵ | 1.2 × 10⁶ | 5.6 × 10⁶ |
| 14 | 1.3 × 10⁶ | 8.7 × 10⁶ | 2.4 × 10⁸ | 2.7 × 10⁸ |
| 21 | 3.5 × 10⁶ | 3.4 × 10⁹ | 5.0 × 10⁸ | 7.1 × 10⁸ |

EXAMPLE 14

Capacity of EPS to Promote Adhesion of Arthrobacter sp. FA-17 Cells to n-hexadecane The capacity of EPS to induce adhesion of bacterial cells to hydrocarbons was measured with the test of E. Rosenberg et al. [Infect. Immun., 39, 1024–1028 (1983)]. This test consists in vigorously stirring a cellular suspension with a certain quantity of n-hexadecane and measuring the number of cells which remain attached to the water-oil interface by measuring the decrease in turbidity of the suspension.

For this purpose an isolated colonial unit of the strain Arthrobacter sp. FA-17 (Eniricerche Collection) was taken from a maintenance culture on Nutrient Aga (Oxoid, CM 003B) and used as inoculum of a subculture in a flask, in 50 ml of Brain Hearth Infusion Broth (Oxoid, CM 225B).

0.1 ml of broth were removed from this subculture, incubated for a night in an orbital stirrer at 30° C. and 150 rpm, for a further inoculum of a culture in a 125 ml flask containing 50 ml of Brain Hearth Infusion Broth. The flask was maintained in the orbital stirrer for 18 hours at 30° C. and 150 rpm until the stationary growth phase was reached. The cells were then collected by centrifugation, washed and resuspended twice with 50 ml of PUM buffer solution (containing per liter: $K_2HPO_4 \cdot 3H_2O$ 22.2 g; $K_2PO_4$ 7.25 g; Urea 1.8 g; $MgSO_4 \cdot 7H_2O$ 0.2 g; pH 7.1).

Aliquots of washed cells were then resuspended in PUM buffer (end volume 4 ml) in four boronsilicate glass tubes (14×140 mm) in various ratios to give extinction values at 400 nm of 0 to 1.5. 0.2 ml of a solution containing 2.1 mg/ml of raw EPS and 1 ml of n-hexadecane were then added to all the tubes. Four duplicates were prepared in the same way with the same concentration of cells and again containing 1 ml of n-hexadecane, but, instead of EPS, 0.2 ml of buffer; only 4.2 ml of buffer and 1 ml of n-hexadecane were introduced into another tube, which acted as blank. The tubes were stirred with a vortex mixer for 120 seconds and then left to rest for 15 minutes in an oven thermostat-regulated at 30° C. to allow the water/hydrocarbon phases to separate. The aqueous phase was removed from each tube and its optical density was measured at 400 nm. The results are indicated in table 8.

TABLE 8

| Sample | Cells (UFC) | Adhesion with EPS (%) | Adhesion without EPS (%) |
|---|---|---|---|
| 1 | $0.5 \times 10^6$ | 89 | 28 |
| 2 | $1 \times 10^7$ | 60 | 24 |
| 3 | $2 \times 10^7$ | 51 | 22 |
| 4 | $4 \times 10^7$ | 44 | 17 |

EXAMPLE 15

Capacity of EPS to Promote the Adhesion of Marine bacterial flora

To determine the capacity of EPS to promote the adhesion of endogenous marine bacterial flora to n-hexadecane, an experiment analogous to that of example 13 was carried out, but using a mixed culture or isolated bacteria from a sample of sea water taken from Ostia Lido (Rome)

For this purpose, 0.1 ml of sea water, immediately after removal, was inseminated by spatulation on the surface of an agarized culture medium with soybean triptone-peptone (OXOID CM 131), containing NaCl 24 g/l.

The grown colonies were collected with a sterile loop in PUM buffer, in a 19×180 mm bacteriological tube, until cellular suspensions of a suitable concentration were obtained.

The measurement of the adhesion of the cells to n-hexadecane was effected as.described in example 14. The results are indicated in table 9.

TABLE 9

| Sample | Cells (UFC) | Adhesion with EPS (%) | Adhesion without EPS (%) |
|---|---|---|---|
| 1 | $1 \times 10^5$ | 76 | 0 |
| 2 | $1 \times 10^6$ | 68 | 17 |
| 3 | $2 \times 10^6$ | 52 | 25 |
| 4 | $4 \times 10^6$ | 38 | 15 |

We claim:

1. A lipopolysaccharide biosurfactant wherein the lipopolysaccharide consists of a polysaccharide chain consisting essentially of 2-amino-2,6 dideoxyaldohexose sugar and glucosamine and one or more non-aminated sugars, wherein the aminic groups of the aminated sugars are all or substantially all in acetylated form, and wherein said polysaccharide chain is bound with an ester bond to a lipid fraction consisting of saturated and/or unsaturated acid radicals with a length of the lipophilic chain of 10 to 18 carbon atoms of which 95–50% consists of dodecanoic acid and 3-hydroxy-dodecanoic acid and wherein the dodecanoic acid is present in an amount greater than 3-hydroxy-dodecanoic acid.

2. The biosurfactant according to claim 1, wherein the polysaccharide chain consists of 70–80% of 2-amino-2,6 dideoxyaldohexose, 5–10% of glucosamine and 15–20% of one or more aminated sugars.

3. The biosurLactant according to claim 1, wherein the dodecanoic acid forms 70–80% of the lipid fraction.

4. The biosurfactant according to claim 1 which further comprises proteins.

5. A biologically pure culture of a strain of *Acinetobacter calcoaceticus* which produces a lipopolysaccharide biosurfactant comprising protein molecules wherein the lipopolysaccharide consists of a polysaccharide chain consisting essentially of 2-amino-2,6 dideoxyaldohexose sugar and glucosamine and one or more non-aminated sugars, wherein the aminic groups of the aminated sugars are all or substantially all in acetylated form, and wherein said polysaccharide chain is bound with an ester bond to a lipid fraction consisting of saturated and/or unsaturated acid radicals with a length of the lipophilic chain of 10 to 18 carbon atoms of which 95–50% consists of dodecanoic acid and 3-hydroxy-dodecanoic acid and wherein the dodecanoic acid is present in an amount greater than the 3-hydroxy-dodecanoic acid.

6. The strain of *Acinetobacter calcoaceticus* according to claim 5, which is *Acinetobacter calcoaceticus* CBS 962.97.

7. A process for the preparation of a lipopolysaccharide biosurfactant comprising protein molecules wherein the lipopolysaccharide consists of a polysaccharide chain consisting essentially of 2-amino-2,6 dideoxyaldohexose sugar and glucosamine and one or more non-aminated sugars, wherein the aminic groups of the aminated sugars are all or substantially all in acetylated form, and wherein said polysaccharide chain is bound with an ester bond to a lipid fraction consisting of saturated and/or unsaturated acid radicals with a length of the lipophilic chain of 10 to 18 carbon atoms of which 95–50% consists of dodecanoic acid and 3-hydroxy-dodecanoic acid and wherein the dodecanoic acid is present in an amount greater than the 3-hydroxy-dodecanoic acid, wherein said process comprises:

(a) culturing a biologically pure culture of a strain of *Acinetobacter calcoaceticus* which produces said lipopolysaccharide biosurfactant in a culture medium containing a source of carbon, nitrogen, phosphorus sulfur and mineral salts; and (b) removing the cells from the culture medium and recovering an acellular product possessing emulsifying activity.

8. The process according to claim 7, wherein the strain is *Acinetobacter calcoaceticus* CBS 962.97.

9. The process according to claim 7, wherein the culture in step a) is carried out at a temperature ranging from 25 to 37° C.

10. The process according to claim 9, wherein the temperature ranges from 28 to 32° C.

11. The process according to claim 7, wherein the culture in step a) is carried out at a pH ranging from 6.5 to 7.5.

12. The process according to claim 11, wherein the pH ranges from 6.8 to 7.2.

13. The process according to claim 7, wherein after removing microbic cells (step b) the lipopolysaccharide biosurfactant is purified and isolated from the fermentation medium.

14. The process according to claim 13, wherein the purification is carried out by selective precipitation with ammonium sulfate, concentration and desalification of the fermentation broth by means of spiral ultrafiltration membranes, or selective absorption on a solid carrier.

15. The process according to claim 13, wherein the purified lipopolysaccharide biosurfactant is deproteinized.

16. A compositionc ontaining the lipopolysaccharidic biosurfactant according to claim 1.

17. A method for biodegradation of hydrocarbons in water, comprising contacting water comprising hydrocarbons with a lipopolysaccharide biosurfactant according to claim 1.

18. The method according to claim 17, wherein said hydrocarbon is a crude oil.

19. The method according to claim 18, wherein said water is sea water.

20. The method according to claim 18, wherein said water is internal water.

21. A method for adhesion stimulation of microbic cells to a water-oil interface of hydrocarbons in water, comprising contacting said hydrocarbons in the presence of water comprising microbic cells with a lipopolysaccharide biosurfactant according to claim 1.

22. A method for forming and stabilizing an oil/water emulsion, comprising contacting hydrocarbons in water with a lipopolysaccharide according to claim 1.

* * * * *